US009894757B2

(12) United States Patent
Arora et al.

(10) Patent No.: US 9,894,757 B2
(45) Date of Patent: Feb. 13, 2018

(54) EXTREMELY STRETCHABLE ELECTRONICS

(71) Applicant: MC10, Inc., Lexington, MA (US)

(72) Inventors: William J. Arora, Bellevue, WA (US); Roozbeh Ghaffari, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 15/337,389

(22) Filed: Oct. 28, 2016

(65) Prior Publication Data

US 2017/0110417 A1 Apr. 20, 2017

Related U.S. Application Data

(63) Continuation of application No. 14/488,544, filed on Sep. 17, 2014, now Pat. No. 9,516,758, which is a
(Continued)

(51) Int. Cl.
| | |
|---|---|
| *H05K 1/02* | (2006.01) |
| *H01L 23/00* | (2006.01) |
| *H05K 1/18* | (2006.01) |
| *H05K 3/32* | (2006.01) |
| *H01L 23/528* | (2006.01) |

(Continued)

(52) U.S. Cl.
CPC ....... *H05K 1/0283* (2013.01); *H01L 23/3121* (2013.01); *H01L 23/528* (2013.01); *H01L 23/564* (2013.01); *H01L 25/16* (2013.01); *H05K 1/189* (2013.01); *H05K 3/326* (2013.01)

(58) Field of Classification Search
CPC ..... H05K 1/028; H05K 1/0281; H05K 1/0283
See application file for complete search history.

(56) References Cited

U.S. PATENT DOCUMENTS

| 3,716,861 A | 2/1973 | Root |
| 3,805,427 A | 4/1974 | Epstein |

(Continued)

FOREIGN PATENT DOCUMENTS

| CN | 202068986 U | 12/2011 |
| DE | 10 2007 046 886 A1 | 4/2009 |

(Continued)

OTHER PUBLICATIONS

U.S. Appl. No. 12/968,637, filed Dec. 15, 2010, J. Rogers, High-Speed, High-Resolution Electrophysiology In-Vivo Using Conformal Electronics.

(Continued)

*Primary Examiner* — Jeremy C Norris
(74) *Attorney, Agent, or Firm* — Nixon Peabody LLP

(57) ABSTRACT

In embodiments, the present invention may attach at least two isolated electronic components to an elastomeric substrate, and arrange an electrical interconnection between the components in a boustrophedonic pattern interconnecting the two isolated electronic components with the electrical interconnection. The elastomeric substrate may then be stretched such that the components separate relative to one another, where the electrical interconnection maintains substantially identical electrical performance characteristics during stretching, and where the stretching may extend the separation distance between the electrical components to many times that of the unstretched distance.

23 Claims, 8 Drawing Sheets

Related U.S. Application Data continuation of application No. 13/767,262, filed on Feb. 14, 2013, now Pat. No. 9,012,784, which is a continuation of application No. 12/616,922, filed on Nov. 12, 2009, now Pat. No. 8,389,862, which is a continuation-in-part of application No. 12/575,008, filed on Oct. 7, 2009, now Pat. No. 9,289,132.

(60) Provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.
　　*H01L 25/16* (2006.01)
　　*H01L 23/31* (2006.01)

(56) References Cited

U.S. PATENT DOCUMENTS

| | | |
|---|---|---|
| 3,838,240 A | 9/1974 | Schelhorn |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 4,911,169 A | 3/1990 | Ferrari |
| 5,059,424 A | 10/1991 | Cartmell |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,265,090 B1 | 7/2001 | Nishide |
| 6,282,960 B1 | 9/2001 | Samuels |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,450,026 B1 | 9/2002 | Desarnaud |
| 6,455,931 B1 | 9/2002 | Hamilton |
| 6,567,158 B1 | 5/2003 | Falcial |
| 6,626,940 B2 | 9/2003 | Crowley |
| 6,628,987 B1 | 9/2003 | Hill |
| 6,641,860 B1 | 11/2003 | Kaiserman |
| 6,775,906 B1 | 8/2004 | Silverbrook |
| 6,784,844 B1 | 8/2004 | Boakes |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,332,053 B1 | 12/2012 | Patterson |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,324,733 B2 | 4/2016 | Rogers |
| 9,372,123 B2 | 6/2016 | Li |
| 9,408,305 B2 | 8/2016 | Hsu |
| 2001/0012918 A1 | 8/2001 | Swanson |
| 2001/0021867 A1 | 9/2001 | Kordis |
| 2002/0000813 A1 | 1/2002 | Hirono |
| 2002/0026127 A1 | 2/2002 | Balbierz |
| 2002/0082515 A1 | 6/2002 | Campbell |
| 2002/0094701 A1 | 7/2002 | Biegelsen |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0248312 A1 | 11/2005 | Cao |

(56) References Cited

U.S. PATENT DOCUMENTS

| | | |
|---|---|---|
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0179373 A1 | 8/2007 | Pronovost |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0030167 A1 | 2/2010 | Thirstrup |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0140856 A1 | 6/2011 | Downie |
| 2011/0140897 A1 | 6/2011 | Purks |
| 2011/0175735 A1 | 7/2011 | Forster |
| 2011/0184320 A1 | 7/2011 | Shipps |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0150693 A1 | 6/2013 | D'Angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0253285 A1 | 9/2013 | Bly |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0328219 A1 | 12/2013 | Chau |
| 2013/0331914 A1 | 12/2013 | Lee |
| 2014/0001058 A1 | 1/2014 | Ghaffari |
| 2014/0012160 A1 | 1/2014 | Ghaffari |

(56) References Cited

U.S. PATENT DOCUMENTS

| | | |
|---|---|---|
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0303680 A1 | 10/2014 | Donnelly |
| 2014/0308930 A1 | 10/2014 | Tran |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Elolampi |
| 2015/0342036 A1 | 11/2015 | Fastert |
| 2016/0027834 A1 | 1/2016 | de Graff |
| 2016/0045162 A1 | 2/2016 | De Graff |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |

FOREIGN PATENT DOCUMENTS

| | | |
|---|---|---|
| EP | 0585670 A2 | 3/1994 |
| EP | 0779059 A1 | 6/1997 |
| EP | 1808124 A2 | 7/2007 |
| EP | 2259062 A2 | 12/2010 |
| JP | 05-087511 A | 4/1993 |
| JP | 2005-052212 A | 3/2005 |
| JP | 2009-170173 A | 7/2009 |
| WO | WO 1999/038211 A2 | 7/1999 |
| WO | WO 2005/076452 A1 | 8/2005 |
| WO | WO 2005/122285 A2 | 12/2005 |
| WO | WO 2003/021679 A2 | 3/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |

OTHER PUBLICATIONS

U.S. Appl. No. 13/492,636, filed Jun. 8, 2012, J. Rogers, Flexible and Stretchable Electronic Systems for Epidermal Electronics.

U.S. Appl. No. 14/155,010, filed Jan. 14, 2014, R. Nuzzo, Methods and Devices for Fabricating and Assembling Printable Semiconductor Elements.

U.S. Appl. No. 14/479,100, filed Sep. 5, 2014, J. Rogers, Printed Assemblies of Ultrathin, Microscale Inorganic Light Emitting Diodes for Deformable and Semitransparent Displays.

U.S. Appl. No. 14/521,319, filed Oct. 22, 2014, J. Rogers, Stretchable and Foldable Electronic Devices.

U.S. Appl. No. 14/706,733, filed May 7, 2015, J. Rogers, Stretchable and Foldable Electronic Devices.

U.S. Appl. No. 15/084,211, filed Mar. 29, 2016, R. Nuzzo, Methods and Devices for Fabricating and Assembling Printable Semiconductor Elements.

U.S. Appl. No. 15/084,091, filed Mar. 29, 2016, R. Nuzzo, Methods and Devices for Fabricating and Assembling Printable Semiconductor Elements.

(56) References Cited

OTHER PUBLICATIONS

U.S. Appl. No. 15/339,338, filed Oct. 31, 2016, J. Rogers, A Stretchable Form of Single Crystal Silicon for High Performance Electronics on Rubber.
U.S. Appl. No. 15/084,112, filed Mar. 29, 2016, J. Rogers, Controlled Buckling Structures in Semiconductor Interconnects and Nanomembranes for Stretchable Electronics.
U.S. Appl. No. 15/217,121, filed Jul. 22, 2016, B. Litt, Flexible and Scalable Sensor Arrays for Recording and Modulating Physiologic Activity.
U.S. Appl. No. 14/004,408, filed Mar. 9, 2012, R. Ghaffari et al., Integrated Devices to Facilitate Quantitative Assays and Diagnostics.
U.S. Appl. No. 13/481,843, filed May 27, 2012, B. Elolampi et al., Electronic, Optical and/or Mechanical Apparatus and Systems and Methods for Fabricating Same.
U.S. Appl. No. 13/499,626, filed Jun. 12, 2012, R. Ghaffari et al., Protective Cases With Integrated Electronics.
U.S. Appl. No. 13/568,022, filed Aug. 6, 2012, R. D'angelo et al., Catheter Balloon Methods and Apparatus Employing Sensing Elements.
U.S. Appl. No. 13/603,290, filed Sep. 4, 2012, C. Rafferty et al., Electronics for Detection of a Condition of Tissue.
U.S. Appl. No. 13/631,739, filed Sep. 28, 2012, C. Rafferty et al., Electronics for Detection of a Property of a Surface.
U.S. Appl. No. 13/646,613, filed Oct. 5, 2012, R. Ghaffari et al., Cardiac Catheter Employing Conformal Electronics for Mapping.
U.S. Appl. No. 13/844,399, filed Mar. 15, 2013, S. Fastert et al., Conformal Electronics Integrated with Apparel.
U.S. Appl. No. 13/844,508, filed Mar. 15, 2013, S. Fastert et al., Monitoring Hit Count for Impact Events.
U.S. Appl. No. 13/844,635, filed Mar. 15, 2013, R. Ghaffari et al., Catheter Balloon Having Stretchable Integrated Circuitry and Sensor Array.
U.S. Appl. No. 13/844,638, filed Mar. 15, 2013, C. Rafferty et al., Embedding Thin Chips in Polymer.
U.S. Appl. No. 13/844,677, filed Mar. 15, 2013, S. Lee et al., Catheter Device Including Flow Sensing.
U.S. Appl. No. 13/844,767, filed Mar. 15, 2013, R. Ghaffari et al., Catheter Balloon Employing Force Sensing Elements.
U.S. Appl. No. 14/276,413, filed May 13, 2014, Y. Hsu et al., Conformal Electronics Including Nested Serpentine Interconnects.
U.S. Appl. No. 14/294,808, filed Jun. 3, 2014, I. Kacyvenski et al., Motion Sensor and Analysis.
U.S. Appl. No. 14/311,686, filed Jun. 23, 2014, J. Fenuccio et al., Band with Conformable Electronics.
U.S. Appl. No. 14/488,544, filed Sep. 17, 2014, W. Arora et al., Extremely Stretchable Electronics.
U.S. Appl. No. 14/510,868, filed Oct. 9, 2014, B. Ives, Utility Gear Including Conformal Sensors.
U.S. Appl. No. 29/506,439, filed Oct. 15, 2014, X. Li et al., Electronic Device Having Antenna.
U.S. Appl. No. 14/518,856, filed Oct. 20, 2014, R. Ghaffari et al., Systems, Methods, and Devices Using Stretchable or Flexible Electronics for Medical Applications.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.
U.S. Appl. No. 14/630,335, filed Feb. 24, 2015, B. Keen, Conformal Electronics with Deformation Indicators.
U.S. Appl. No. 14/656,046, filed Mar. 12, 2015, R. Ghaffari et al., Quantification of a Change in Assay.
U.S. Appl. No. 14/726,136, filed May 29, 2015, R. Ghaffari et al., Catheter Balloon Methods and Apparatus Employing Sensing Elements.
U.S. Appl. No. 14/726,142, filed May 29, 2015, R. Ghaffari et al., Cardiac Catheter Employing Conformal Electronics for Mapping.
U.S. Appl. No. 14/746,659, filed Jun. 22, 2015, S. Fastert et al., Conformal Electronics Integrated With Apparel.

U.S. Appl. No. 14/758,946, filed Jul. 1, 2015, S. Fastert et al., Application for Monitoring a Property of a Surface.
U.S. Appl. No. 14/812,197, filed Jul. 29, 2015, B. De Graff et al., Methods and Applications of Non-Planar Imaging Arrays.
U.S. Appl. No. 14/819,040, filed Aug. 5, 2015, Elolampi et al., A Method for Fabricating a Flexible Electronic Structure and a Flexible Electronic Structure.
U.S. Appl. No. 14/838,196, filed Aug. 27, 2015, G. Callsen et al., Methods and Apparatus for Conformal Sensing of Force and/or Acceleration at a Person's Head.
U.S. Appl. No. 14/859,112, filed Sep. 18, 2015, C. Rafferty et al., Embedded Thin Chips in Polymer.
U.S. Appl. No. 14/859,680, filed Sep. 21, 2015, D. Garlock, Methods and Apparatuses for Shaping and Looping Bonding Wires That Serve as Stretchable and Bendable Interconnects.
U.S. Appl. No. 14/870,719, filed Sep. 30, 2015, M. Dalal et al., Flexible Electronic Circuits with Embedded Integrated Circuit Die and Methods of Making and Using the Same.
U.S. Appl. No. 14/870,802, filed Sep. 30, 2015, M. Dalal et al., Flexible Interconnects for Modules of Integrated Circuits and Methods of Making and Using the Same.
U.S. Appl. No. 14/874,148, filed Oct. 2, 2015, Stephen P. Lee, Catheter Device Including Flow Sensing.
U.S. Appl. No. 14/924,440, filed Oct. 27, 2015, Bassel De Graff, Systems, Methods, and Devices Having Stretchable Integrated Circuitry for Sensing and Delivering Therapy.
U.S. Appl. No. 15/003,644, filed Jan. 21, 2016, Roozbeh Ghaffari et al., Methods of Detecting Parameters of a Lumen.
U.S. Appl. No. 15/016,937, filed Feb. 5, 2016, Jesus Pindado et al., Method and System for Interacting with an Environment.
U.S. Appl. No. 15/047,314, filed Feb. 18, 2016, Roozbeh Ghaffari et al., Catheter or Guidewire Device Including Flow Sensing and Use Thereof.
U.S. Appl. No. 15/047,333, filed Feb. 18, 2016, Roozbeh Ghaffari et al., Catheter or Guidewire Device Including Flow Sensing and Use Thereof.
U.S. Appl. No. 15/048,576, filed Feb. 19, 2016, Shyamal Patel et al., Automated Detection and Configuration of Wearable Devices Based on-Body Status, Location, and/or Orientation.
U.S. Appl. No. 15/057,762, filed Mar. 1, 2016, Brian Murphy et al., Perspiration Sensor.
U.S. Appl. No. 15/023,556, filed Mar. 21, 2016, Roozbeh Ghaffari, Conformal Sensor Systems for Sensing and Analysis.
U.S. Appl. No. 15/139,256, filed Apr. 26, 2016, Xia Li et al., Flexible Temperature Sensor Including Conformable Electronics.
U.S. Appl. No. 15/038,401, filed May 20, 2016, Huppert et al., Conformal Sensor Systems for Sensing and Analysis of Cardiac Activity.
U.S. Appl. No. 15/183,513, filed Jun. 15, 2016, Wang et al., Moisture Wicking Adhesives for Skin-Mounted Devices.
U.S. Appl. No. 15/194,995, filed Jun. 28, 2016, Hsu et al., Strain Isolation Structures for Stretchable Electronics.
U.S. Appl. No. 15/208,444, filed Jul. 12, 2016, McGrane et al., Conductive Stiffener, Method of Making a Conductive Stiffener, and Conductive Adhesive and Encapsulation Layers.
U.S. Appl. No. 15/238,488, filed Aug. 16, 2016, Sun et al., Wearable Heat Flux Devices and Methods of Use.
U.S. Appl. No. 15/272,816, filed Sep. 22, 2016, Pindado et al., Method and System for Crowd-Sourced Algorithm Development.
U.S. Appl. No. 15/281,960, filed Sep. 30, 2016, Ghaffari et al., Method and System for Interacting with a Virtual Environment.
U.S. Appl. No. 15/286,129, filed Oct. 5, 2016, Ghaffari et al., Method and System for Neuromodulation and Stimulation.
U.S. Appl. No. 15/337,389, filed Oct. 28, 2016, Arora et al, Extremely Stretchable Electronics.
U.S. Appl. No. 15/108,861, filed Jun. 29, 2016, McMahon et al, Encapsulated Conformal Electronic Systems and Devices, and Methods of Making and Using the Same.
Carvalhal et al., "Electrochemical Detection in a Paper-Based Separation Device", Analytical Chemistry, vol. 82, No. 3, (1162-1165) (4 pages) (Jan. 7, 2010).

(56) References Cited

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX. No. 15, 1119-1126. (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Mehl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Wikipedia, "Ball bonding" article [online]. Cited in PCT/US2015/051210 search report dated Mar. 1, 2016 with the following information "Jun. 15, 2011 [retrieved on Nov. 15, 2015}. Retrieved 12-18, 29 from the Internet: <URL: https://web.archive.org/web/20110615221003/http://en.wikipedia.org/wiki/Ball_bonding>., entire document, especially para 1, 4, 5, 6," 2 pages, last page says ("last modified on May 11, 2011").

Bossuyt et al., "Stretchable Electronics Technology for Large Area Applications: Fabrication and Mechanical Characterizations", vol. 3, pp. 229-235 (7 pages) (Feb. 2013).

Jones et al., "Stretchable Interconnects for Elastic Electronic Surfaces". vol. 93, pp. 1459-1467 (9 pages) (Aug. 2005).

Lin et al., "Design and Fabrication of Large-Area, Redundant, Stretchable Interconnect Meshes Using Excimer Laser Photoablation and in Situ Masking", (10 pages) (Aug. 2010).

Kim et al., "A Biaxial Stretchable Interconnect With Liquid-Alloy-Covered Joints on Elastomeric Substrate", vol. 18, pp. 138-146 (9 pages) (Feb. 2009).

European Search Report corresponding to co-pending European Patent Application Application Serial No. EP 15157473.8, European Patent Office, dated Sep. 15, 2015; (7 pages).

European Search Report corresponding to co-pending European Patent Application Serial No. EP 15157469.6, European Patent Office, dated Sep. 15, 2015; (6 pages).

Canadian Office Action corresponding to co-pending Canadian Patent Application Serial No. CA 2,780,747, Canadian Patent Office, dated Jan. 11, 2016; (7 pages).

EXTREMELY STRETCHABLE ELECTRONICS

CROSS-REFERENCE TO RELATED APPLICATIONS

This application is a continuation of U.S. application Ser. No. 14/488,544, filed Sep. 17, 2014, now issued as U.S. Pat. No. 9,516,758, which is a continuation of U.S. application Ser. No. 13/767,262, filed Feb. 14, 2013, now issued as U.S. Pat. No. 9,012,784, which is a continuation of U.S. application Ser. No. 12/616,922, filed Nov. 12, 2009, now issued as U.S. Pat. No. 8,389,862, which claims priority to and the benefit of U.S. Provisional Application No. 61/113,622, entitled "Extremely Stretchable Interconnects," filed on Nov. 12, 2008; U.S. application Ser. No. 12/616,922 is a continuation-in-part of U.S. application Ser. No. 12/575,008, entitled "Catheter Balloon Having Stretchable Integrated Circuitry and Sensor Array," filed on Oct. 7, 2009, now issued as U.S. Pat. No. 9,289,132, which claims priority to and the benefits of U.S. Provisional Application Nos. 61/103,361, filed Oct. 7, 2008, and 61/113,007, filed Nov. 10, 2008; all of the foregoing applications are hereby incorporated by reference herein in their entireties.

FIELD OF THE INVENTION

The present invention relates to systems, apparatuses, and methods utilizing expandable or stretchable integrated circuitry, and more particularly to extremely stretchable integrated circuitry.

BACKGROUND OF THE INVENTION

The field of stretchable electronics continues to grow due to the demand of high performance and mechanically unconstrained applications of the future. However, stretchable electronics have been thus far limited in stretchability. This has limited the ability of stretchable electronics to accommodate applications that require more extreme stretchability. Therefore a need exists for extremely stretchable electronics.

SUMMARY OF THE INVENTION

This invention is for extremely stretchable electrical interconnects and methods of making the same. In embodiments, the invention comprises a method of making stretchable electronics, which in some embodiments can be out of high quality single crystal semiconductor materials or other semiconductor materials, that are typically rigid. For example, single crystal semiconductor materials are brittle and cannot typically withstand strains of greater than about +/−2%. This invention describes a method of electronics that are capable of stretching and compressing while withstanding high translational strains, such as in the range of −100,000% to +100,000%, and/or high rotational strains, such as to an extent greater than 180°, while maintaining electrical performance found in their unstrained state.

In embodiments, the stretching and compressing may be accomplished by fabricating integrated circuits (ICs) out of thin membrane single crystal semiconductors, which are formed into "islands" that are mechanically and electrically connected by "interconnects," and transferring said ICs onto an elastomeric substrate capable of stretching and compressing. The islands are regions of non-stretchable/compressible ICs, while the interconnects are regions of material formed in a way to be highly stretchable/compressible. The underlying elastomeric substrate is much more compliant than the islands, so that minimal strain is transferred into the islands while the majority of the strain is transferred to the interconnects, which only contain electrical connections and not ICs. Each interconnect attaches one island to another island, and is capable of accommodating strain between the two aforementioned islands, including translation, rotation, or a combination of translation with rotation of one island relative to another. Even though the interconnects may be made of a rigid material, they act like weak springs rather than rigid plates or beams. This configuration thereby allows for the making of extremely stretchable electronics.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE DRAWINGS

The invention and the following detailed description of certain embodiments thereof may be understood by reference to the following figures:

FIG. 6A is a side view of device islands and extremely stretchable interconnects transferred onto an elastomeric substrate. In this case, the substrate has been molded to have posts that are of the same area as the device islands (note that in embodiments these could be smaller or larger than the device islands). The height "h" of the molded post regions may range from, but is not limited to, about 1-1000 μm. The interconnects are located in between these regions as shown. FIG. 6B is a side view as before, with a similarly shaped elastomeric superstrate to serve as an encapsulation layer protecting the devices from direct mechanical contact.

While the invention has been described in connection with certain preferred embodiments, other embodiments would be understood by one of ordinary skill in the art and are encompassed herein.

All documents referenced herein are hereby incorporated by reference.

DETAILED DESCRIPTION OF THE INVENTION

The present invention accomplishes extremely stretchable electronics by forming the electronics on discrete islands 102 of silicon.

With reference to the present invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable", and roots and derivations thereof, when used to modify circuitry or components thereof is also meant to have the meaning ascribed above. Thus, "stretch" and "expand", and all derivations thereof, may be used interchangeably when referring to the present invention.

In embodiments, the discrete islands mention above are discrete operative (in embodiments, arranged in a "device island" arrangement) and are themselves capable of performing the functionality described herein, or portions thereof. In embodiments, such functionality of the operative devices can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means.

Figure 1:
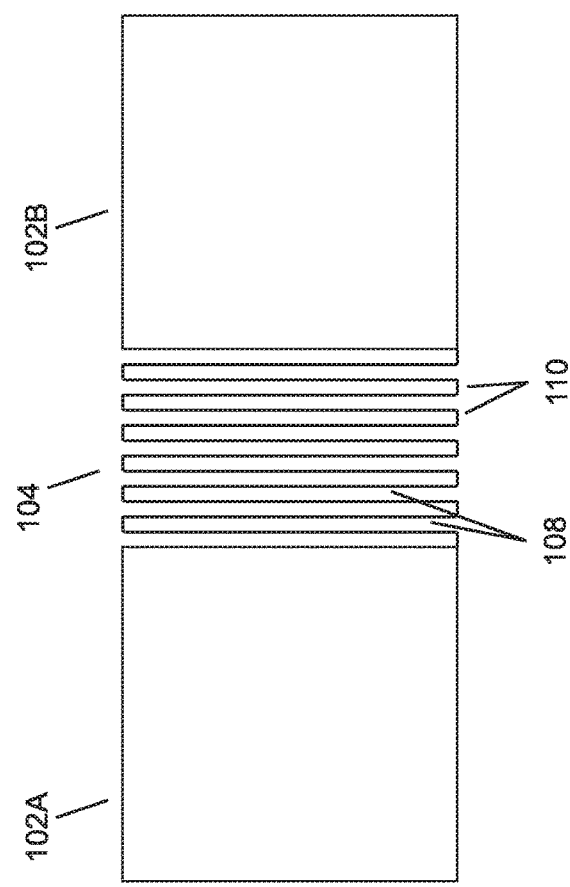
FIG. 1 depicts an overhead view of an embodiment of the present invention showing two device islands connected edge-to-edge by a monolithically formed extremely stretchable interconnect, prior to being stretched.

In an example, the discrete islands 102 may range from about, but not limited to, 10-100 μm in size measured on an edge or by diameter, and connecting said islands 102A-B with one or more extremely stretchable interconnects 104. The novel geometry of the interconnects 104 is what makes them extremely compliant. Each interconnect 104 is patterned and etched so that its structural form has width and thickness dimensions that may be of comparable size (such as their ratio or inverse ratio not exceeding about a factor of 10); and may be preferably equal in size. In embodiments, the dimensions may not be greater than about Sum (e.g. where both dimensions are about 1 μm or less). The interconnect 104 may be formed in a boustrophedonic style such that it effectively comprises long bars 108 and short bars 110 as shown in FIG. 1. This unique geometry minimizes the stresses that are produced in the interconnect 104 when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress.

Figure 2:
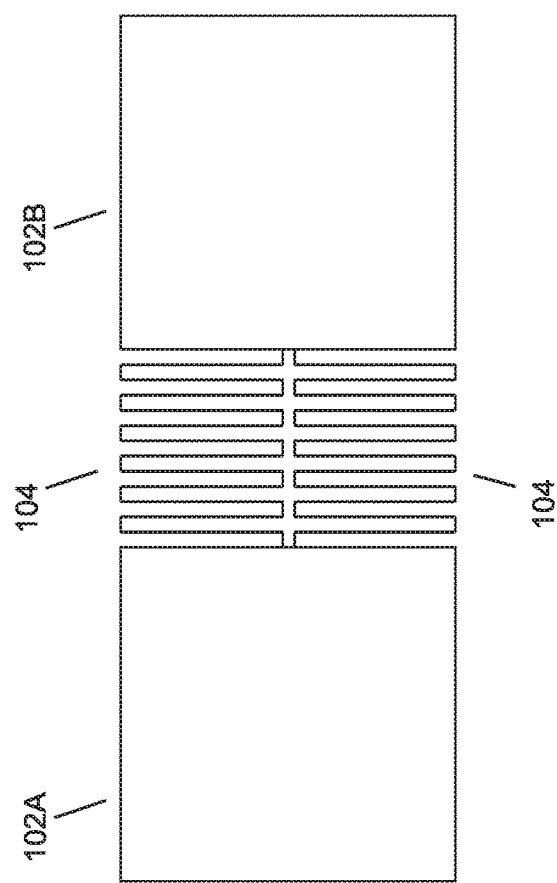
FIG. 2 depicts an overhead view of an embodiment of the present invention showing two device islands connected edge-to-edge by two extremely stretchable interconnects.
Figure 3:
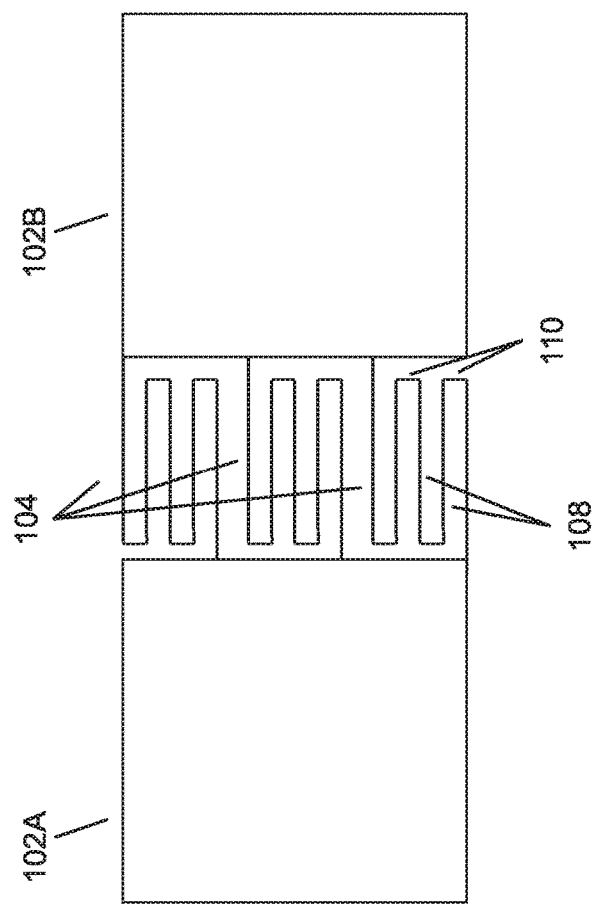
FIG. 3 depicts an overhead view of an embodiment of the present invention showing two device islands connected edge-to-edge by three extremely stretchable interconnects; in this case, the long bars of the interconnects are rotated by 90° which allows them to be longer than if they were not rotated.
Figure 4:
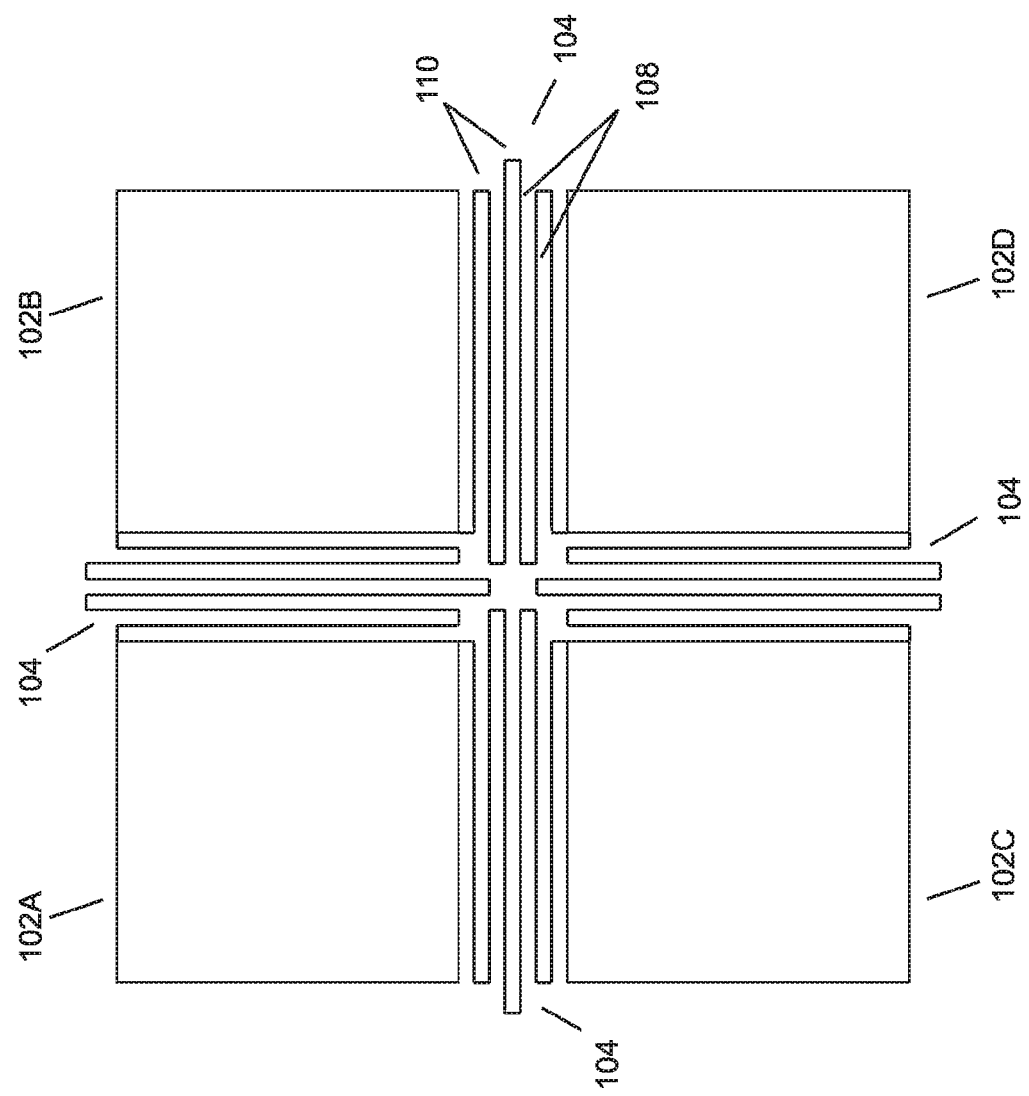
FIG. 4 depicts four device islands arranged in a square matrix in an embodiment of the present invention, with each edge connected by an extremely stretchable interconnect to its nearest neighbors island edge, and the interconnects are formed so as to maximize the amount of chip area that is used for either an island or interconnect.
Figure 5:
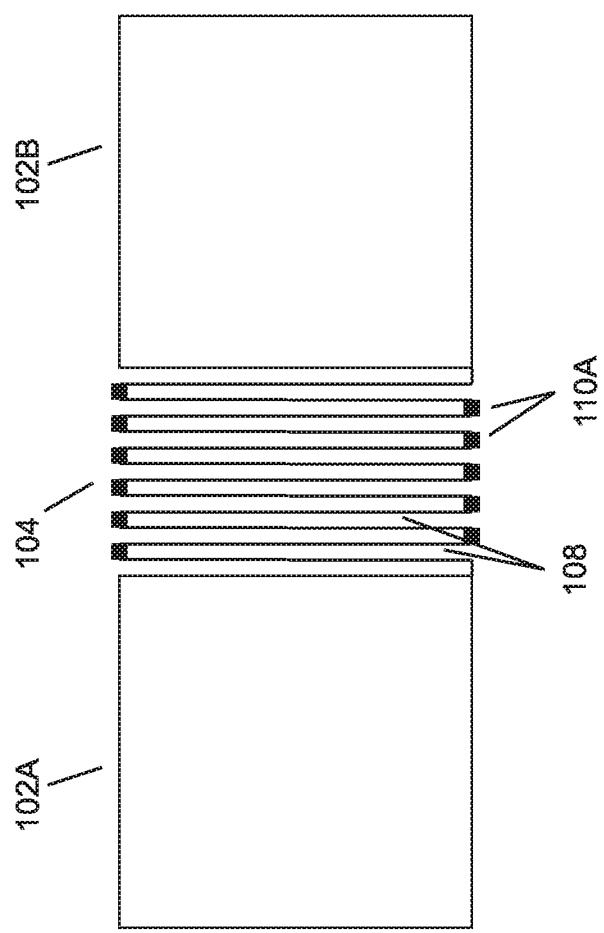
FIG. 5 depicts the case of FIG. 1, with the short bars widened for extra mechanical strength at those locations.

In addition, because the interconnect 104 may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands 102A-B. This is illustrated in FIG. 1. One or more interconnects 104 may be formed in various ways, as shown in FIGS. 2-4. The parts of the interconnect 104 where the majority of stresses build up during stretching may be the short linking bars. To minimize cracking here, the short linking bars 110A may be made several micrometers wider than the longer bars 108, as shown in FIG. 5.

In embodiments, the connection point of the interconnect 104 to the device island 102 may be anywhere along the device island edge, or may be at a point on the surface of the device island 102 (in which case the interconnect may be located just above the plane of the device island).

In embodiments, device islands 102 may be made on any suitable material substrate, provided that a top membrane layer of said substrate that contains the ICs can be freed from the bulk of the substrate and transfer printed onto an elastomeric substrate.

Figure 6:
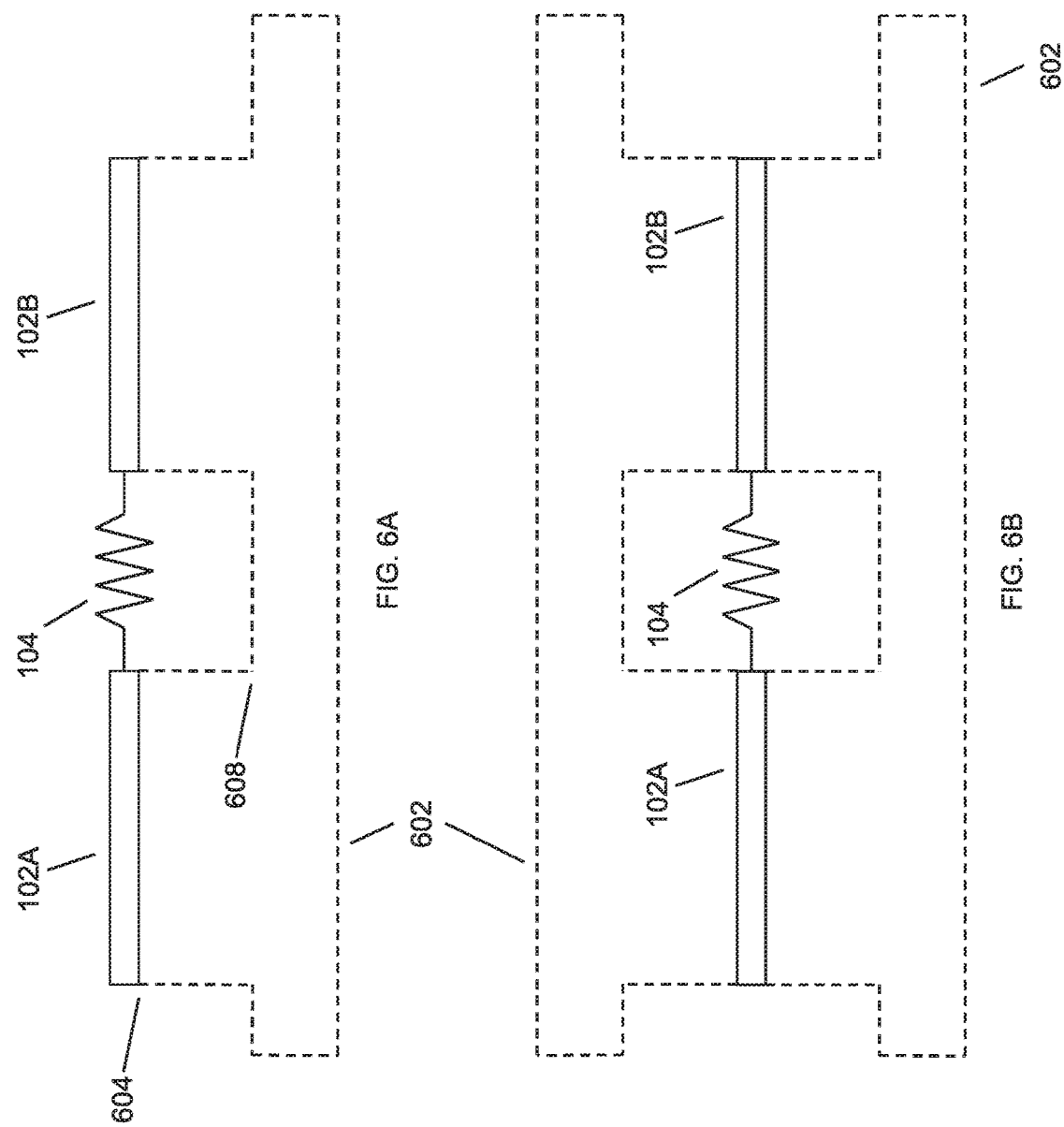
FIGS. 6A and 6B depict embodiments of the present invention, where

In the present invention, the interconnects 104 (as described herein) may be formed either monolithically (i.e., out of the same semiconductor material as the device islands) or may be formed out of another material. In one non-limiting example embodiment, the stretchable electronics are fabricated on a silicon-on-insulator (SOI) wafer, having a 1 μm thick top silicon layer and a 1 μm thick buried oxide layer. Devices are formed on the top silicon wafer, and arranged into a square pattern of islands 102A-D and interconnects 104 of the general form shown in FIG. 4, in which the islands 102 are 100 μm on an edge, and the interconnects 104 are 1 μm wide, and the space between each long bar is 1 μm, and the interconnects 104 comprise 10 long bars 108, all about 100 μm long. The islands 102 and interconnects 104 are formed in an etching step which removes the excess silicon. The islands 102 and interconnects 104 are coated with a 1 μm layer of polyimide that is patterned to only cover the islands 102 and interconnects 104. Next, the islands 102 and interconnects 104 are released in an HF etch which undercuts the underlying buried oxide. After drying, the islands 102 and interconnects 104 are transfer printed with a Polydimethylsiloxane (PDMS) stamp onto an elastomeric substrate 602. After being picked up by the transfer stamp, and prior to being placed onto the elastomeric substrate 602, the backsides of the islands 102 may be coated with a layer of polyimide (patterned to only cover the islands 102 and interconnects 104), and an additional layer of evaporated 3 nm chromium and 30 nm silicon dioxide selectively over the island regions to improve adhesion to the elastomeric substrate 602 at those locations, and not along the interconnects 102. The elastomeric substrate 602 may be PDMS or another highly compliant material. The elastomeric substrate 602 may additionally be molded or etched into the shape shown in FIGS. 6A and 6B, to further increase selective adhesion in the device island region but not the interconnect region, and to reduce the amount of material strain in the elastomeric substrate 602 that is transferred to the device islands 102. In this example, the interconnects may accommodate stretching the device islands apart by approximately up to 800 μm. In addition, the interconnects 104 of this example may be capable of accommodating lateral shear displacements of about 800 μm. In general, they may be capable of accommodating any relative displacement of the two islands such that they remain approximately within 800 μm of each other. In addition, the interconnects 104 may accommodate corkscrew type rotations of one island relative to another about any of the three axes of rotation. This feature may be limited only by the interconnects becoming entangled within each other. In any practical application, the completed stretchable device may not be so severely rotated, and the interconnect may easily accommodate rotations of up to 180°. It is noted that by increasing the number of long bars 108 used in the interconnect 104, or by increasing the length of the long bars 108, the interconnect may be able to accommodate even larger displacement strains. In embodiments, there may be no practical upper limit to the amount of displacement enabled through the present invention.

Figure 7:
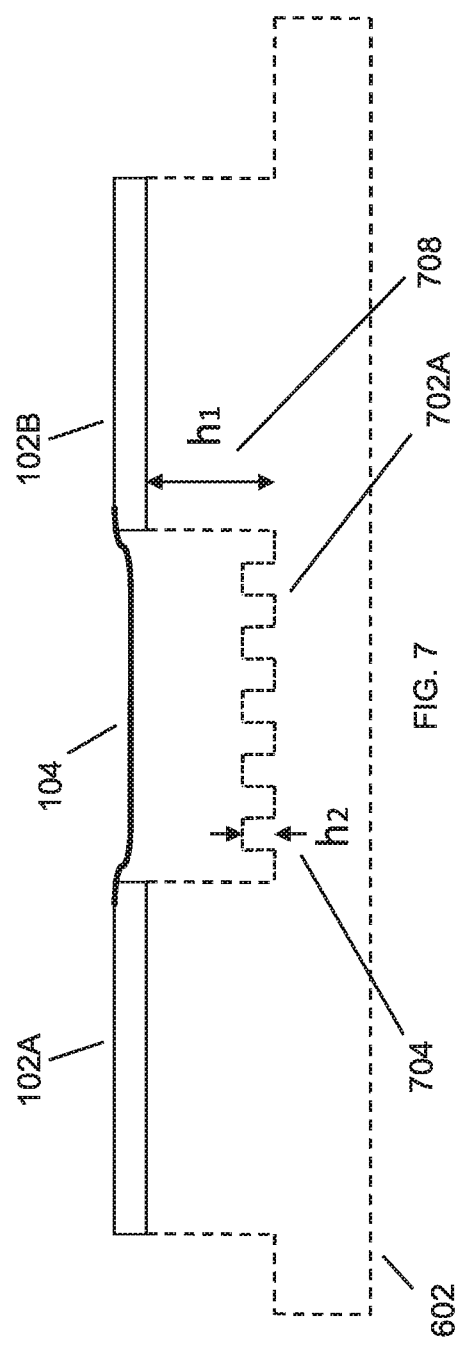
FIG. 7 depicts a side view of a two-layer PDMS substrate in an embodiment of the present invention comprising silicon device islands adhered to top layer, free-standing interconnects, and square wave ripples in the lower layer PDMS to promote increased stretching through the substrate.
Figure 8:
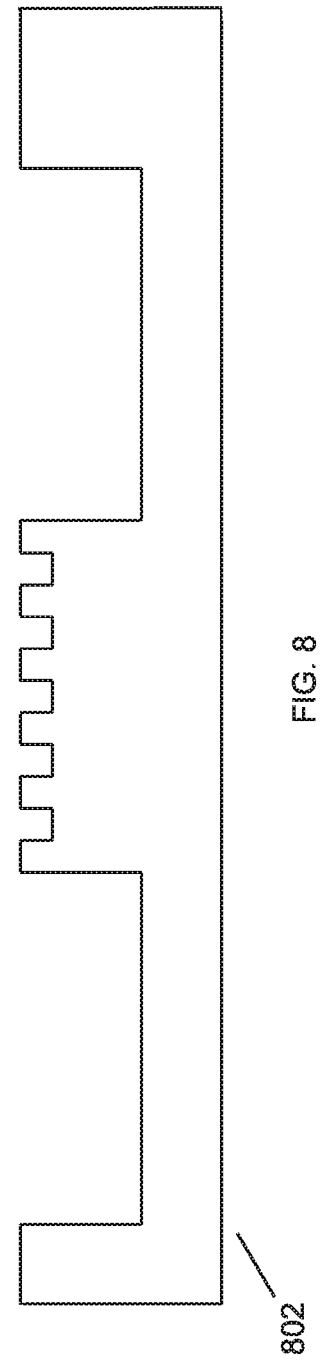
FIG. 8 depicts an embodiment of the present invention with a side view of two layers of cured photoresist (SU-8 50 and SU-8 2002) used to make the two-layer PDMS substrate described in FIG. 7.

In another embodiment the elastomeric substrate 602 may comprise two layers separated by a height. The top "contact" layer contacts the device island 102 as in the embodiment illustrated in FIG. 6. In addition, FIG. 7 shows the bottom layer 702 may be a "wavy" layer containing ripples or square waves molded into the substrate 602 during elastomer fabrication. These square waves enable additional stretching, whose extent depends on the amplitude and wavelength of the waves pattern-molded in the elastomer 602. FIG. 7 shows one non-limiting layout and topology of an elastomeric substrate 602 relative to the position of the interconnects 104 and device islands 102A-B. In an example, a two layer molded substrate can be fabricated using two step process consisting of two types of negative photoresist (SU-8 50 and SU-8 2002; Microchem Corporation). The negative resists can be spin-coated on a transfer silicon wafer with spin speeds of 3000 rpm. The SU-8 50 layer can be spun on the wafer, and subsequently cured with UV radiation. Once the SU-8 50 layer has hardened, the SU-8 2002 can be spun and cured with a photo-mask and an alignment tool. In this example, the thickness of the SU-8 50 and SU-8 2002 are 40-50 μm 708 and 2-10 μm 704, respectively. The 40-50 μm thick regions of SU-8 50 contain ripples 702 of SU-8 2002 (in this instance in the form of square waves) on their surfaces. Upon curing of the SU-8 2002 layer, liquid PDMS can be poured over the SU-8 patterns to form a substrate in the shape of the SU-8 molds 802, as shown in FIG. 8. The amplitude of the ripples in the SU-8 mold 802 can be varied by changing the spin speed used for spinning the thin layer of SU-8 2002. In this configuration, the interconnects 104 are free-standing. The entire substrate-device configuration can be immersed in non-cured elastomer (fluid layer) layer followed by a cured layer of PDMS to encapsulate the fluid and devices.

Figure 9:
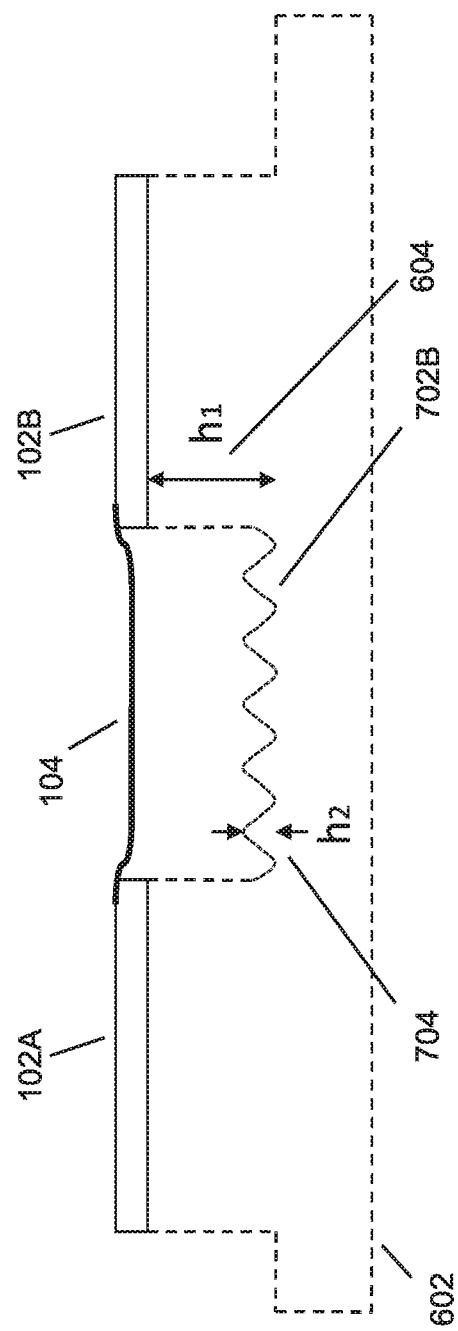
FIG. 9 depicts an embodiment of the present invention with a side view of a two-layer PDMS substrate consisting of sinusoidal waves in the lower layer of PDMS to promote increased stretching through the substrate.

In another embodiment, the PDMS in the lower layer may be designed with periodic sinusoidal ripples 702B. In embodiments, this ripple configuration may be achieved by bonding Si nanoribbons on the surface of pre-strained PDMS in a uniform parallel pattern. The release of the prestrain in the PDMS substrate generates sinusoidal waves along the thin Si-nanoribbons (caused by buckling) and the surface of the PDMS substrate. The amplitude and wavelength of these waves 702B may depend on the extent of uniaxial pre-strain exerted on the PDMS and on the mechanical properties of the Si-nanoribbons. The wavy surface on the PDMS may be used as a transfer mold. Two-part liquid plastic solution can be poured over the wavy PDMS substrate and cured at room temperature over time (~2 hrs). Once the plastic hardens, the plastic substrate can be peeled away from the PDMS. This new plastic transfer substrate with wavy surface features can be used to produce more PDMS substrates containing wave features. The wavy PDMS may serve as the lower layer of PDMS as in the previous embodiment. To produce a two layer PDMS structure, a top layer of PDMS can be plasma bonded to this lower layer of PDMS using oxygen plasma surface activation to produce the substrate illustrated in FIG. 9.

In another embodiment, the PDMS transfer stamp is stretched after the islands 102A-B and interconnects 104 are picked up. A subsequent transfer to another elastomeric substrate 602 may place these pre-stretched devices in a configuration, which allows the new elastomeric substrate to undergo compression. The devices may be able to accommodate that compression because the interconnects are pre-stretched.

In another embodiment, the interconnects 104 are not made out of the same material as the device islands 102. In this case, the islands 102A-B are completely isolated from each other by etching, with no interconnects in between. In an example, a layer of polyimide may then be deposited, contact vias etched to various locations on the surface of the device island 102, and then metal interconnects 104 deposited and patterned into a boustrophedonic pattern, followed by another layer of polyimide. Both layers of polyimide may now be patterned and etched to leave a small border around the interconnects 104 (thereby fully encapsulating the interconnects). These interconnects may have the advantage that they are already fully encapsulated in polyimide and will not adhere as well to the elastomeric substrate as the device islands will. The other advantage is that these interconnects may not be limited to only connecting along the edge of an island. The contact via may be etched anywhere on the surface of the island 102, including near the center. This may allow for easier connections to devices, more connections than possible only along an edge, increased strain compliance, decreased strain at the contact vias, and multiple layers of interconnects made with polymer passivation layers in between, allowing even more interconnects, or allowing one device island 102A to connect to a non-neighboring device island 102B.

In another embodiment of the invention, the device islands 102 are fabricated and transfer printed onto the elastomeric substrate 602, or substrate comprising a polymeric release layer and polymeric non-release layer. After transfer printing, the interconnects 104 are formed as described above, which may be possible because they do not require any high temperature processing, and then in the latter case, the release layer is etched and the devices that are on the non-release layer, are transfer printed onto another elastomeric substrate 602. In the former case, the islands 102 may be transferred onto the elastomeric substrate using pick and place technology so that islands 102 that are initially fabricated very close to each other are spread apart when they are transfer printed. This allows the interconnects 104 to be fabricated in a pattern that resembles their stretched configuration (if desired), to allow compression.

In embodiments, the present invention may comprise a stretchable electrical interconnect 104, including an electrical interconnect 104 for connecting two electrical contacts 102A-B (e.g. device islands 102A-B), where the electrical interconnect 104 may be arranged boustrophedonically to define rungs 108 (i.e. long bars 108) between the contacts 102A-B, and where the rungs 108 may be substantially parallel with one another and where a plurality of rungs 108 may have substantially the same length and displacement therebetween. In addition, the ratio of the length of the plurality of rungs 108 and the displacement between the plurality of rungs 108 may be large, such as at least 10:1, 100:1, 1000:1, and the like. The electrical integrity of the electrical interconnect 104 may be maintained as stretched, such as to displacements that are increased to 1000%, 10000%, 100000%, and the like during stretching. In embodiments, the rungs 108 may be substantially perpendicular to the contacts 102A-B, the interconnection 104 may have a trace width and/or inter-rung spacing ranging between 0.1-10 microns. In embodiments, the two electrical contacts 102A-B may be located on an elastomeric substrate 602, the electrical contacts 102A-B may be bonded to the substrate 602 and the interconnection 104 not bonded to the substrate 602, the electrical contacts 102A-B may be semiconductor circuits, metal contacts, and the like.

In embodiments, the present invention may comprise a stretchable electrical interconnect 104, including an electrical interconnect 104 for connecting two electrical contacts 102A-B, where the electrical interconnect 104 is arranged boustrophedonically to define rungs 108 between the contacts 102A-B, and where the interconnect 104 maintains electrical conductivity and electrical integrity when a displacement between the contacts 102A-B is increased, such as by 1000%, 10000%, 100000%, and the like.

In embodiments, the present invention may electrically interconnect two electrical contacts 102A-B with a stretchable interconnection 104 that has the ability to twist between the two electrical contacts 102A-B by up to approximately 180 degrees while maintaining electrical integrity of the stretchable interconnection 104.

In embodiments, the present invention may be a device including a body having a stretchable surface (e.g. an elastomeric substrate 602), and a stretchable electronic circuit including (i) a first discrete operative device 102A, (ii) a second discrete operative device 102B, and (iii) a stretchable interconnect 104 connecting the first discrete operative device 102A to the second discrete operative device 102B, where the interconnect 104 may have a substantially boustrophedonic pattern and be able to maintain electrical conductivity when stretched, such as up to 1000%, 10000%, 100000%, and the like. The stretchable electronic circuit may be affixed to the stretchable surface of the body. In embodiments, the connection may be to a metal contact, to a semiconductor device, and the like. The first discrete operative device 102A, the second discrete operative device 102B, and the stretchable interconnect 104 may all be made from the same material, and that material may be a semiconductor material.

In embodiments, the present invention may attach at least two isolated electronic components (which in embodiments may be discrete operative devices) 102A-B to an elastomeric substrate 602, and arrange an electrical interconnection 104 between the components 102A-B in a boustrophedonic pattern interconnecting the two isolated electronic components 102A-B with the electrical interconnection 104. The elastomeric substrate 602 may then be stretched such that components 102A-B separate relative to one another, where the electrical interconnection 104 maintains substantially identical electrical performance characteristics that the electrical interconnection 104 had in a pre-stretched form. In embodiments, the stretching may be a translational stretching, where the separation between the isolated electronic components 102A-B increases by a percent as a result of the stretching, such as 10%, 100%, 1000%, 10000%, 100000%, and the like. The stretching may be a rotational stretching, where the rotation may be greater than a certain rotation angle, such as 90°, 180°, 270°, 360°, and the like, where the stretching may be in all three axes. In embodiments, the electrical interconnection 104 may be made from semiconductive material. The electrical interconnection 104 may be made from the same semiconductor material as the isolated electronic components 102A-B, fabricated at the same time as the isolated electronic components 102A-B, and the like. The semiconductor material may be a single crystal semiconductor material. The electrical interconnection 104 may made of a different material than the isolated electronic components 102A-B, such as a metal. In embodiments, the interconnect material 104 may be loosely bound to the elastomeric substrate 602, not connected at all, raised above the surface of the elastomeric substrate 602, and the like. In embodiments, the at least two isolated semiconductor circuits may be fabricated on an upper surface 604 of the elastomeric substrate 602 separated by a lower surface 608 of the elastomeric substrate 602, and the electrical interconnection 104 may be fabricated at the level of the upper surface 604 of the elastomeric substrate 602. In this way, the electrical interconnection 104 may have no direct contact with the lower level 608, and thereby be substantially free from adhesion to the lower level 608 during stretching. In addition, the lower surface 608 of the elastomeric substrate 602 may include a wavy form 702, where the wavy form 704 may allow the elastomeric substrate 602 to expand during stretching.

While the invention has been described in connection with certain preferred embodiments, other embodiments would be understood by one of ordinary skill in the art and are encompassed herein.

All documents referenced herein are hereby incorporated by reference.

What is claimed is:

1. A stretchable integrated circuit (IC) system comprising:
a flexible substrate;
a first device island mounted to the flexible substrate and comprising a first integrated circuit (IC) device fabricated from a rigid semiconductor material;
a second device island mounted to the flexible substrate and comprising a second integrated circuit (IC) device fabricated from a rigid semiconductor material; and
a flexible electrical interconnect electrically connecting the first IC device to the second IC device, such that a distance between the first IC device and the second IC device can be changed while maintaining an electrical connection between the first IC device and the second IC device.

2. The stretchable IC system of claim 1, wherein at least one of the first IC device and the second IC device comprises a physical sensor, a biological sensor, a chemical sensor, a light emitting diode (LED), or any combination thereof.

3. The stretchable IC system of claim 2, wherein the at least one of the first IC device and the second IC device comprises the physical sensor, the physical sensor includes at least one of a temperature sensor, a pH sensor, a light sensor, a radiation sensor, a pressure sensor, and a contact sensor.

4. The stretchable IC system of claim 2, wherein the at least one of the first IC device and the second IC device comprises the biological sensor, the biological sensor includes at least one of an electrophysiological sensor, a skin temperature sensor, and a skin pH sensor.

5. The stretchable IC system of claim 1, wherein at least one of the first IC device and the second IC device comprises an amplifier, a buffer, an A/D converter, a D/A converter, an optical collector, an electro-mechanical transducer, a piezoelectric actuator, or any combination thereof.

6. The stretchable IC system of claim 1, wherein the first IC device comprises a high performance microprocessor and the second IC device comprises a physical sensor, a biological sensor, a chemical sensor, an LED, or any combination thereof.

7. The stretchable IC system of claim 1, wherein the first device island and the second device island are coated in a flexible polymeric material.

8. The stretchable IC system of claim 1, wherein the first device island, the second device island, and the flexible electrical interconnect are encapsulated by a flexible encapsulation layer.

9. The stretchable IC system of claim 1, wherein the flexible substrate, the first device island, the second device island, and the flexible electrical interconnect are encapsulated by a fluid layer, and the fluid layer is encapsulated by a flexible encapsulation layer.

10. The stretchable IC system of claim 1, wherein the first device island and the second device island are adhered to the flexible substrate, and wherein the flexible electrical interconnect lacks adhesion to the substrate.

11. The stretchable IC system of claim 1, wherein the first device island and the second device island are adhered to a first horizontal surface of the flexible substrate and the flexible electrical interconnect is spaced from a second horizontal surface of the flexible substrate.

12. The stretchable IC system of claim 11, wherein the second horizontal surface of the flexible substrate includes a wavy form which permits the flexible substrate to expand during stretching.

13. The stretchable IC system of claim 11, wherein the first device island and the second device island are adhered to a first horizontal surface of a flexible encapsulation layer and the flexible electrical interconnect is spaced from a second horizontal surface of the flexible encapsulation layer, wherein the flexible encapsulation layer encases the first device island, the second device island, and the flexible electrical interconnect between the flexible substrate and the flexible encapsulation layer.

14. The stretchable IC system of claim 1, wherein the flexible electrical interconnect is a single-piece electrically conductive body.

15. The stretchable IC system of claim 1, wherein the distance between the first IC device and the second IC device is increased by 1000%.

16. The stretchable IC system of claim 1, wherein the flexible electrical interconnect is configured to maintain the electrical connection between the first IC device and the second IC device when the first IC device and the second IC device are twisted up to approximately 180 degrees relative to one another.

17. The stretchable IC system of claim 1, wherein the flexible electrical interconnect is configured to maintain the electrical connection between the first IC device and the second IC device when the flexible electrical interconnect is stretched by 1000%.

18. The stretchable IC system of claim 1, wherein the flexible electrical interconnect is configured to maintain the electrical connection between the first IC device and the second IC device when the flexible substrate is subjected to a translational stretching or a rotational stretching.

19. The stretchable IC system of claim 13, wherein responsive to the translational stretching of the flexible substrate, the distance between the first IC device and the second IC device is increased by 1000%.

20. The stretchable IC system of claim 13, wherein responsive to the rotational stretching of the flexible substrate, the first IC device and the second IC device are rotated up to approximately 180 degrees relative to one another.

21. The stretchable IC system of claim 1, wherein the flexible electrical interconnect is made from a semiconductor material.

22. The stretchable IC system of claim 18, wherein the semiconductor material of the flexible electrical interconnect is the same or substantially the same as the rigid semiconductor material.

23. The stretchable IC system of claim 1, wherein the first IC device and the second IC device each comprises a thin membrane semiconductor having a width or diameter of about 10-100 micrometers (μm).

* * * * *